United States Patent [19]

Wallshein

[11] 4,197,642
[45] Apr. 15, 1980

[54] BENT WIRE ORTHODONTIC SPRING CLIP

[76] Inventor: Melvin Wallshein, 8645 Bay Pkwy., Brooklyn, N.Y. 11214

[21] Appl. No.: 837,725

[22] Filed: Sep. 29, 1977

[51] Int. Cl.² .................................................. A61C 7/00
[52] U.S. Cl. ....................................................... 433/11
[58] Field of Search ......................................... 32/14 A

[56] References Cited
U.S. PATENT DOCUMENTS

| | | | |
|---|---|---|---|
| 1,976,115 | 10/1934 | Boyd et al. | 32/14 A |
| 3,256,602 | 6/1966 | Broussard et al. | 32/14 A |
| 3,772,787 | 11/1973 | Hanson | 32/14 A |

Primary Examiner—Robert Peshock
Attorney, Agent, or Firm—Frishauf, Holtz, Goodman & Woodward

[57] ABSTRACT

An orthodontic spring clip is made of bent wire and comprises a first portion which is preferably formed of at least two spaced elongated members, adapted to engage over at least a part of a portion of a bracket having an arch wire receiving opening therein, and to pass over at least a portion of the arch wire receiving opening of the bracket in order to retain an arch wire in the opening relative to the bracket. The spring clip further comprises a second portion comprised of at least two elongated members coupled to the first portion of the clip and adapted to engage the bracket with the first portion of the clip at least partially covering the arch wire receiving opening of the bracket. Further, means is provided for coupling together the elongated members of at least one of the first and second clip portions. Further disclosed are specific spring clip arrangements and novel bracket constructions having means cooperating with orthodontic spring clips.

114 Claims, 62 Drawing Figures

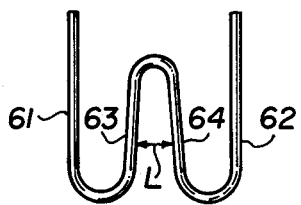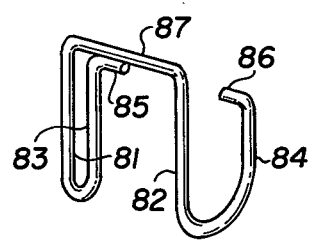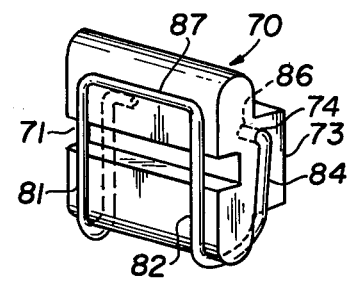
FIG.13  FIG.14  FIG.15
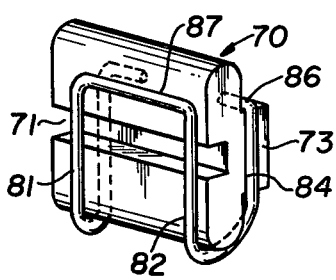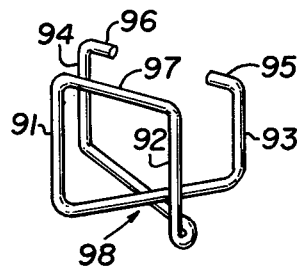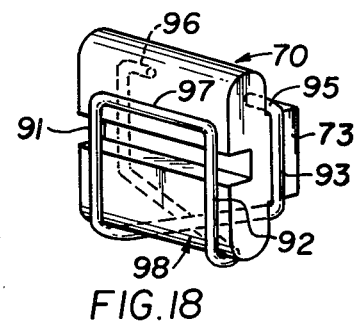
FIG.16  FIG.17  FIG.18
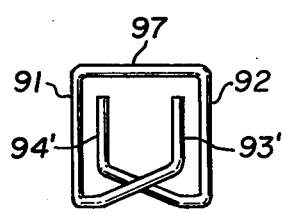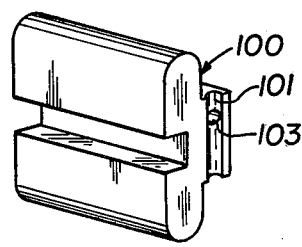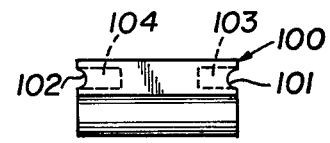
FIG.19  FIG.20  FIG.21
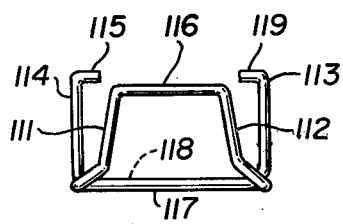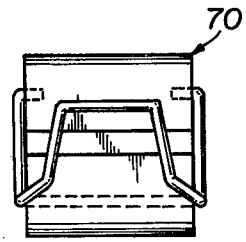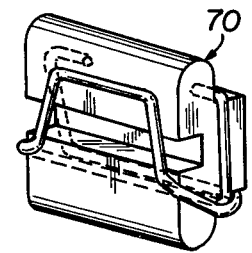
FIG.22  FIG.23  FIG.24

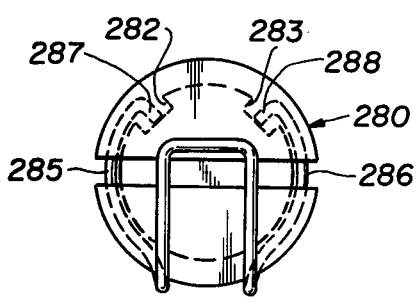
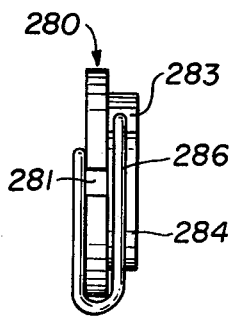
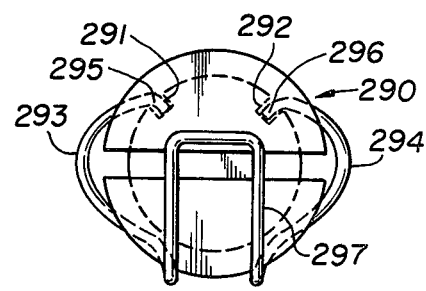
FIG.49  FIG.50  FIG.51
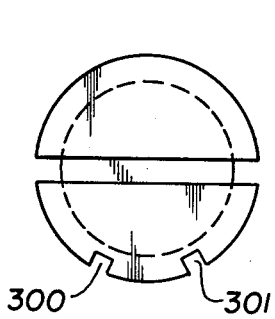
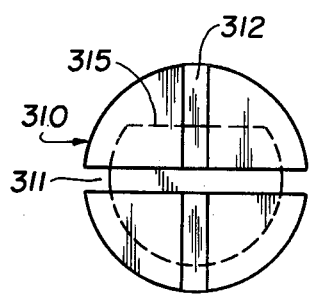
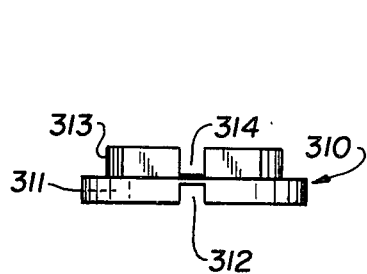
FIG.52  FIG.53  FIG.54
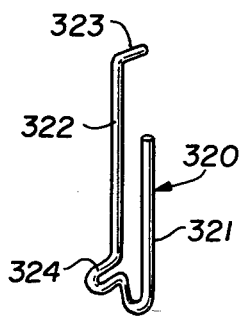
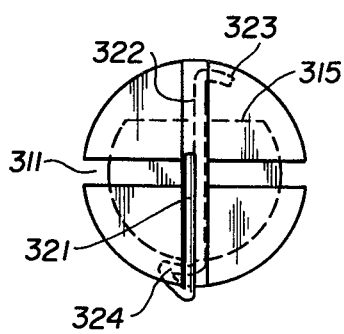
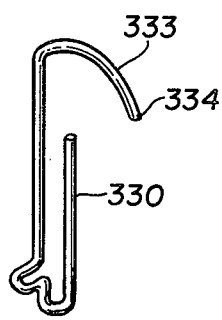
FIG.55  FIG.56  FIG.57
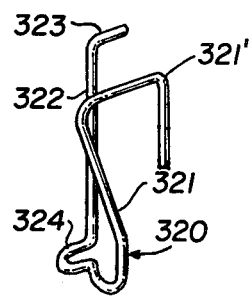
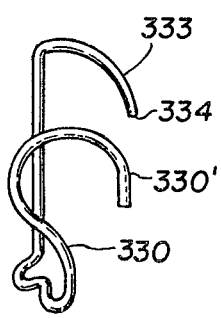
FIG.59  FIG.58

BENT WIRE ORTHODONTIC SPRING CLIP

The present invention relates to improvements in orthodontic spring clips which are to be used in association with an orthodontic bracket, or the like. More particularly, the invention is directed to bent wire spring clips which are intended to retain an arch wire in engagement with an orthodontic bracket, or the like.

Generally speaking, orthodontic procedures involve the securing of an orthodontic bracket to a maloccluded tooth, the bracket having a channel for receiving an arch wire therein. In order to properly confine the arch wire within the channel of the bracket, tie wires have been utilized. A disadvantage of tie wires is that they are non-resilient in nature and that they are not easily installed on a bracket and that they are not easily removable therefrom without cutting same. Further disadvantages of tie wires are well known and are discussed in, for example, column 1 of my prior U.S. Pat. No. 3,871,096, issued Mar. 18, 1975.

Various orthodontic spring clips are known, for example my prior spring clips disclosed in said U.S. Pat. No. 3,871,096 and in my prior U.S. Pat. No. 3,835,539. The object of the present invention, however, is to provide a still further improved and easy to manufacture orthodontic spring clip for use, for example, in connection with orthodontic brackets for retaining an arch wire, or the like, relative to the orthodontic bracket, the spring clip being made of a bent wire.

It is a further object of the present invention to provide an orthodontic spring clip which is usable to mount auxiliaries to the bracket, or the like, in a simple and expedient manner without requiring substantial increases in complexity and cost of the spring clip.

A still further object of the invention is to provide an orthodontic spring clip which is completely and simply removable from the orthodontic bracket.

Another object of the invention is to provide orthodontic spring clips which utilize torsion-bending effects to provide good resilience to facilitate installation and insertion, and which also provide high arch wire retention forces.

Another object of the present invention is to provide a simple to manufacture orthodontic spring clip which is fabricated of wire, or the like, and which contacts the arch wire in the bracket at two spaced positions therealong so as to permit the resultant bracket, arch wire and spring clip assembly to impart rotational forces to a tooth.

Another object of the invention is to provide a wire orthodontic spring clip with arch wire engaging means to permit the spring clip to apply orthodontic forces to a tooth relative to an arch wire.

Yet another object of the invention is to provide improved orthodontic brackets for use with wire spring clips according to the present invention as well as for use with other spring clips.

A still further object of the invention is to provide wire orthodontic spring clips which may be moved relative to the bracket to free the arch wire receiving opening and which will then spring back into position covering the arch wire receiving opening of the bracket.

SUMMARY OF THE INVENTION

In accordance with one aspect of the present invention, a bent wire orthodontic clip for use with an orthodontic bracket means having an arch wire receiving opening comprises a front portion adapted to engage over at least a part of a portion of the bracket having the arch wire receiving opening, and to pass over at least a portion of the arch wire receiving opening to retain an arch wire relative to the bracket, said front portion including at least two spaced elongated members passing over the arch wire receiving opening. The clip further comprises a second portion, preferably comprised of at least two elongated members, coupled to the front portion of the clip and adapted to engage the bracket with the front portion of the clip at least partially covering the arch wire receiving opening of the bracket. Means is further provided for coupling together the elgonated members of at least the first clip portion.

In a preferred embodiment, the spring clip of the present invention includes means to permit movement of the spring clip relative to the bracket without being fully disengaged from the bracket so as to permit access to the arch wire opening of the bracket.

Further, according to the present invention, various novel brackets are provided for use with orthodontic spring clips.

According to a further aspect of the invention, an orthodontic spring clip made of bent wire for use with an orthodontic bracket means having an arch wire receiving opening comprises a first wire portion adapted to engage over at least a part of a portion of a bracket having said arch wire receiving opening, and to pass over at least a portion of said arch wire receiving opening to retain an arch wire relative to said bracket; and a second wire portion coupled to said first wire portion and adapted to engage said bracket with said first wire portion at least partially covering said arch wire receiving opening of the bracket. The first and second wire portions comprises means movable relative to said bracket so as to permit said first wire portion to less than completely pass over said arch wire receiving opening to permit removal and insertion of an arch wire, or the like, in said arch wire receiving opening of the bracket. The clip further comprises engagement means engaging at least a portion of the bracket to prevent said clip from becoming disengaged from said bracket during movement of said clip relative to said bracket to insert or remove an arch wire, or the like, from the arch wire receiving opening of the bracket.

BRIEF DESCRIPTION OF THE DRAWINGS

FIG. 13 illustrates a further modified embodiment of the present invention;

FIG. 14 illustrates a still further modified embodiment of the present invention;

FIGS. 15 and 16 illustrate the general embodiment of FIG. 14 mounted on respective brackets;

FIG. 17 illustrates a still further modification of the present invention;

FIG. 18 illustrates the embodiment of FIG. 17 mounted on a bracket;

FIG. 19 illustrates an embodiment modified from that of FIG. 17;

FIGS. 20 and 21 illustrate perspective and top views, respectively, of a modified bracket for use with the present invention;

FIG. 22 illustrates yet another embodiment of the present invention;

FIGS. 23 and 24 are front and perspective views, respectively, showing the spring clip of FIG. 22 mounted on a bracket;

FIGS. 49 and 50 show front and side views of round orthodontic brackets and spring clips of the present invention;

FIG. 51 illustrates another embodiment of a spring clip for use with a round bracket;

FIG. 52 illustrates a modified round bracket of the present invention;

FIGS. 53–56 show a further modified bracket and spring clip in accordance with the present invention;

FIG. 57 illustrates a modification of the spring clip shown in FIGS. 55 and 56;

FIGS. 58 and 59 illustrate respective modifications of the clips of FIGS. 57 and 55.

DETAILED DESCRIPTION

Figure 1:
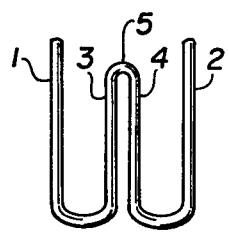
FIG. 1 is a front view of an orthodontic spring clip according to the present invention.

In the following description of preferred embodiments, it is pointed out that all of the spring clips of the present invention are fabricated of bent wire, preferably each being made of a single piece of bent wire. The wire is springy in nature so that it is capable of providing spring action. The wires are shown as having round cross-sections, but any cross-sectional shape could be used. Preferably the wire, when round, has a cross-sectional diameter from about 0.005 to 0.028 inches, and more preferably from about 0.010 to 0.011 inches. Other shapes preferably have a largest cross-sectional dimension not greater than about 0.028 inches. Rectangular wires having cross-sections of about $0.005 \times 0.010$ inches have been found to be suitable. Stainless steel wires, such as 304 Stainless Steel (1800 Series), of diameter 0.011 inches, have been found to be particularly useful. Nitinol wire (a nickel-titanium wire developed by the Naval Ordinance Laboratory) is also suitable. Nickel-cobalt and nickel-chromium wires can also be used. With reference to Nitinol wire, reference is made to U.S. Pat. No. 4,037,324, the entire contents of which is incorporated herein by reference.

Spring wires used in the present invention are characterized by a fibrous structure resulting from the wire drawing, particularly cold drawing. The wire in the as drawn condition, particularly the small wire size contemplated, is fibrous with an elongated grain or fiber structure which is oriented in the direction of drawing, i.e., the longitudinal direction of the wire. The wire must be bent during fabrication and, therefore, should be sufficiently soft to permit the requisite bending. With the available materials this contemplates heat treatment of the wire so that it may be fabricated (bent) into the desired shape followed by a subsequent heat treatment to harden the wire.

A unique characteristic of the wire used in the present invention is that even after such heat treatment, the wire continues to exhibit the above described fibrous or grain structure with consequent anisotropic properties. When the wire is bent, the fibrous structure follows the bend and the resulting bent structure is highly resilient and springy, as required for an orthodontic spring clip. The fibrous structure follows the length of the wire and if the wire is tortuously bent, the fiber structure follows the tortuous bends.

The present invention is also useful with amorphous spring wires, that is, wires which do not have an ordered crystal structure. These wires, when formed and heat treated if necessary, exhibit a high degree of springiness and ultimate strength which enable them to be advantageously used in the present invention.

By virtue of the fact that a wire is used as the structural element for the spring clip of the present invention, e.g., as opposed to flat spring metal, a high degree of retaining force can be applied to an orthodontic arch wire, or the like, without requiring an excessively wide spring clip. The forces obtained with the bent wire-type spring clip of the present invention are concentrated and the resultant wire structure has greater resistance to breakage during use in the mouth than the clips made of e.g., flat spring metal. The wire used in the present invention also has the characteristic such that when set up next to a metal bracket or the like, no electrical currents are generated and no chemical reactions occur. Also no chemical reactions occur when used with plastic brackets.

Figure 2:
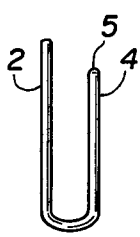
FIG. 2 is a side view of the spring clip of FIG. 1.

Referring to FIG. 1, an orthodontic spring clip comprises first and second elongated front members 1,2 and first and second elongated rear members 3,4. The clip of FIG. 1 is preferably made of a wire having some resiliency. The elongated members 1,2 are shown in FIG. 1 as having free ends and respective opposite ends integrally connected with the elongated members 3,4 which are interconnected at 5. Preferably, the clip of FIG. 1 is fabricated from a single piece of wire which is appropriately bent. A side view of the clip is shown in FIG. 2 and a perspective view of the clip mounted on a bracket is shown in FIG. 3.

Figure 3:
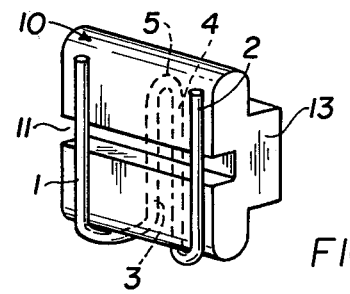
FIG. 3 illustrates the spring clip of FIG. 1 mounted on a bracket, in perspective.
Figure 4:
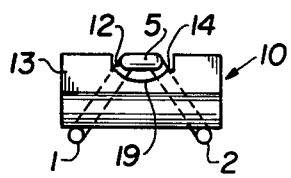
FIG. 4 is a top view of the bracket and clip arrangement of FIG. 3.

Referring to FIG. 3, an orthodontic bracket 10 has an arch wire receiving opening 11 therein. The arch wire is not shown so as not to unduly complicate the illustration. The rear legs 3,4 of the spring clip are inserted into a slot 12 (see FIG. 4) in the base portion 13 of the orthodontic bracket 10. The rear legs 3,4 may be biassed toward the front legs 1,2 so that the entire structure is engaged in the bracket with the rear legs springing against the inner surface 14 of the rear slot 12 in the bracket. The front elongated members 1,2 are sprung against the front face of the bracket 10. See FIG. 4.

In most of the embodiments of the invention, the wire portions are arranged relative to each other so as to make use of torsional bending effects. This is particularly advantageous since torsional bending permits greater bending of the spring clip to take place without causing permanent deformation thereof. This renders the spring clip of the present invention less prone to fatigue in use.

Figure 5:
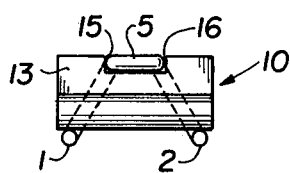
FIG. 5 is a top view of a modified arrangement similar to that of FIG. 3.

In an alternative arrangement, the rear legs 3,4 of the spring clip are spaced apart so that when they are inserted in the rear opening 12 of the bracket, the legs 3,4 springingly engage against the side walls 15,16 of the opening 12 in the bracket 10. This alternative arrangement is illustrated in FIG. 5. The biassed type spring clip described above in connection with FIGS. 1-5 engage the bracket with sufficient force to maintain them in position merely by means of the biassing created by the resiliency of the wire from which the spring clip is formed. Alternatively, less resilient materials could be used and other locking means, such as bending over a portion of the clip, could be used to retain same engaged with a bracket, or the like. However, bending over portions of the clip is less desirable than using the spring biassed engagement techniques discussed above.

Figure 6:
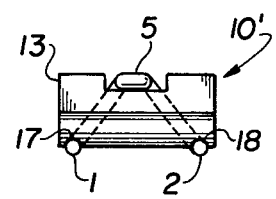
FIG. 6 is a top view of a further modification of the arrangement shown in FIG. 3.

FIG. 6 illustrates a modified orthodontic bracket which is particularly suitable for use with a spring clip according to the present invention. The front surface of the bracket has grooves 17,18 formed therein for receiving the front legs 1,2 of a spring clip of the present invention. The grooves 17,18 enhance the retaining characteristics of the spring clip of the present invention. Moreover, when an arch wire which does not completely fill the arch wire receiving opening 11 of the bracket is used, the grooves 17,18 enable the front legs 1,2 of the spring clip to enter a portion of the arch wire receiving opening 11 so as to press the smaller arch wire deeply into the arch wire receiving opening to prevent excessive play of the arch wire relative to the bracket.

Figure 7A:
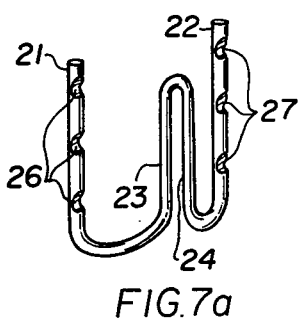
FIGS. 7a and 7B are modified orthodontic spring clips according to the present invention.

FIG. 7a illustrates a modified spring clip according to the present invention. In the embodiment of FIG. 7a, the two front legs 21,22 of the spring clip have respective cut-outs 26,27. The rear legs 23,24 generally correspond to the rear legs 3,4 described above with respect to FIGS. 1-5. In a typical example, the middle cut-outs 26,27 may be arranged so as to be in registration with the arch wire receiving opening 11 of the bracket 10. This enhances engagement of the spring clip with an arch wire which is received in the opening 11. When a bracket with front grooves 17,18 is used, the middle cut-outs 26,27 are particularly advantageous, especially when an arch wire which completely fills the opening 11 is used. The remaining cut-outs 26,27 may be used to engage an arch wire which is not possible to insert into the arch wire receiving opening 11 during a particular stage of orthodontic treatment. For example, during a stage in orthodontic treatment, it is possible that an arch wire may not quite reach the opening 11. In this event, for example the upper cut-outs 26,27 could be used to engage the arch wire, with the spring clip engaged with a bracket 10, so as to apply orthodontic forces to the tooth on which the orthodontic bracket 10 is mounted. The resiliency of the spring clip of the present invention enables same to be sprung away from the first surface of a bracket in order to receive an arch wire between a front surface of the bracket (other than the opening 11) and the cut-out portions 26,27. It has been found that the cut-out portions 26,27 are sufficient to provide positive engagement of the arch wire to apply orthodontic forces to a maloccluded tooth. As treatment progresses, the forces applied via the cut-outs 26,27 and the arch wire will cause the tooth to move into a position whereby the arch wire can be inserted into the bracket opening 11. At this point, the arch wire can merely be snapped from the engagement in upper cut-outs 26,27 into the arch wire receiving opening 11 of the bracket for retention therein by the spring clip. These procedures can all be performed without removal of the spring clip of the present invention from the bracket, thereby simplifying procedures. Similar effects can be obtained with the lower cut-outs 26,27. Under certain circumstances, it may be advisable to utilize tie wires to retain the arch wire in the openings 26,27 when the arch wire does not quite reach the arch wire receiving opening 11 of the bracket 10.

Figure 7B:
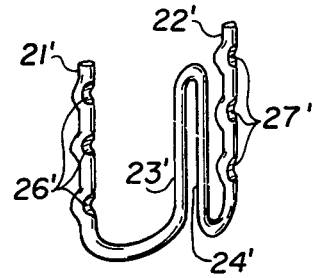

FIG. 7b illustrates a clip similar to that of FIG. 7a but wherein the front legs 21',22' have outwardly extending portions 26',27', respectively, which correspond to cut-out portions 26,27 of FIG. 7a. The outwardly directed wire engaging portions 26',27' may be formed by a bending or an impacting operation, or any other suitable operation.

The cut-outs 26,27 or bent-out portions 26',27' of FIGS. 7a and 7b additionally provide clearance between the arch wire and the spring clip so as to avoid friction or contact between the arch wire and the spring clip. This feature is particularly advantageous when the front surfaces of the bracket are grooved to recess the clip, as shown in FIG. 6. In such a case, a full size arch wire can be used without contact with the spring clip, even through the spring clip is recessed in the front surface of the bracket.

Figure 8:
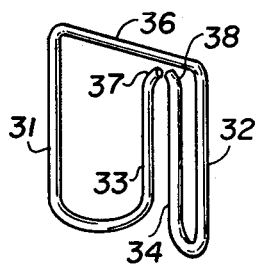
FIGS. 8 and 9 are perspective views of respective further modifications of the spring clip of the present invention.

FIG. 8 illustrates a further embodiment of the present invention wherein the front leg portions 31,32 are joined at the upper ends by means of a cross member 36 which is preferably integral with leg members 31,32. Rear leg members 33,34 are preferably integral with respective front legs 31,32 and comprise bent-over portions 37,38, respectively. The bent-over portions 37,38 enable easier insertion of the rear legs 33,34 into a rear bracket opening 12. In side view, the embodiment of FIG. 8 appears substantially similar to that of FIG. 2. Preferably, the clip of FIG. 8 is made of a single piece of resilient wire material.

Figure 9:
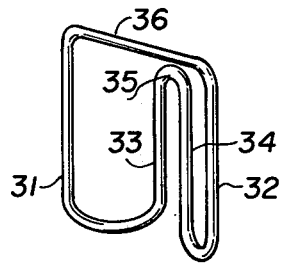

FIG. 9 illustrates an embodiment similar to that of FIG. 8 except that the legs 33,34 are joined at 35, similar to legs 3 and 4 of FIG. 1. In all other respects, the embodiment of FIG. 9 is substantially similar to that of FIG. 8.

Figure 10:
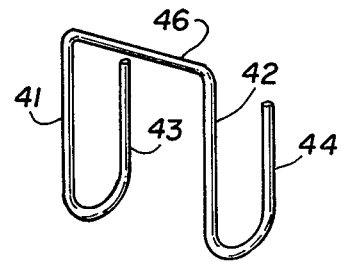
FIG. 10 is a perspective view of a further modified embodiment of the invention.

FIG. 10 illustrates a further embodiment of the present invention which comprises front leg portions 41,42 joined at the top by a cross portion 46, which is preferably integral with leg portions 41,42. Rear leg members 43,44 respectively extend from front legs 41,42 and are adapted to be received in rear openings of a bracket, for example as shown in FIG. 11.

Figure 11:
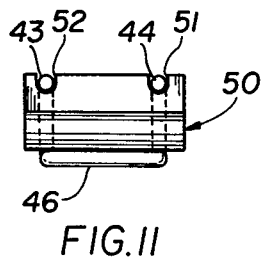
FIG. 11 illustrates the embodiment of FIG. 10 mounted on a bracket.

Referring to FIG. 11, a bracket 50 with rear openings 51,52 is adapted to receive the rear legs 43,44 of the spring clip shown in FIG. 10. The spring clip of FIG. 10 is preferably configured so that the respective pairs of front and rear legs 41-43, 42-44 are spring biassed towards each other so that the clip is springingly engaged in the bracket 50. The bracket of FIG. 11 may be modified as in FIG. 6 so as to provide grooves for at least partially recessing the front portions of the spring clip in the bracket. As mentioned with respect to FIG. 6, this enhances retention of smaller arch wires in the arch wire receiving opening 11 of a bracket.

It should be clear that the spring clips of FIGS. 8-10 may be provided with cut-outs or bend-outs similar to the cut-outs 26,27 and bend-outs 26',27' shown in the embodiments of FIGS. 7a and 7b, respectively, with the same resultant effects.

Figure 12:
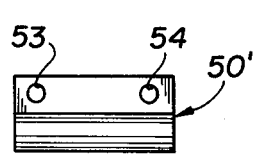
FIG. 12 illustrates a modified bracket for use with spring clips along the lines of FIG. 10.

In the embodiment of FIG. 11, the openings 51,52 are shown formed from the rear surface of the bracket 50. As shown in FIG. 12, the openings for receiving the rear legs 43,44 of a spring clip may be formed through other portions of the bracket 50', as exemplified by the openings 53,54. In use, the rear legs 43,44 of the embodiment of FIG. 10 are inserted through openings 53,54, the front portion 41,42,46 overlying the front face of the bracket 50', similarly to FIG. 11.

FIG. 13 illustrates an embodiment of the invention similar to that of FIG. 1. In FIG. 13, the distance "L" between the rear legs 63,64 is relatively large. In use, the user of the spring clip will pinch the rear legs 63,64 together, by means of for example pliers, so that the rear legs 63,64 may be inserted into various different types of brackets having different types of openings for receiving the rear legs 63,64, or to vary the distance between the front legs 61,62 to adapt to a particular bracket arrangement. The front legs 61,62 are similar to front legs 1,2 shown in FIGS. 1-5. In side view, the embodiment of FIG. 13 is substantially similar to the view shown in FIG. 2.

FIGS. 14 and 15 illustrate a further modified spring clip according to the present invention, FIG. 15 illustrating the clip in use on a bracket. Referring to FIG. 14, the spring clip comprises front leg portions 81,82 interconnected by a cross portion 87. The rear legs 83,84 are integral with front legs 81,82 and extend rearwardly and outwardly with respect to the front legs 81,82 as seen in FIG. 15. The rear legs 83,84 include bent-over portions 85,86 for engagement in a clip receiving opening of a bracket.

Referring to FIG. 15, a bracket 70 having an arch wire receiving opening 71 is illustrated with a clip of FIG. 14 installed thereon. The bent-over portion 86 of the clip is inserted into the clip receiving opening 74 formed therein. The opening 74 need not be formed in the base portion 73, but may be formed in any other side portion of the bracket 70 for use with the clip of FIG. 14. The left side of bracket 70 has a clip receiving opening (not shown) for receiving the bent-over portion 85 of leg 83.

The spring clip of FIG. 14 may be used as shown in FIG. 16 when the rear legs 83,84 are lengthened so that the bent-over portions 85,86 can be engaged over an edge of the base portion 73 of the bracket 70. Engaging means for an end, for example 86, of a rear leg of the spring clip can be varied, as desired.

FIG. 17 illustrates a further embodiment of the invention wherein the rear leg portions 93,94 cross at a rear portion of the clip, for example at 98, and extend upwardly with bracket engaging bent-over portions 95,96. FIG. 18 illustrates the spring clip of FIG. 17 installed on a bracket. In FIG. 18 the bent-over portion 95 is shown engaged around the upper surface of the bracket base 73. However, a clip receiving opening, for example like opening 74 in FIG. 15, may be provided to receive a bent-over portion 95 when the leg 93 is shortened somewhat.

FIG. 19 illustrates a further embodiment of the present invention, similar to that of FIG. 17, except that the rear legs 93',94' do not extend outwardly of the front legs 91,92 and are particularly adapted to be received in bracket openings, such as openings 51,52 shown in FIG. 11 or openings 53,54 shown in FIG. 12. The spacing between the legs 93,94 may be varied, as desired, depending upon the spacing between the holes in the brackets which receive the legs 93',94'.

While the embodiments of FIGS. 17 and 19 are somewhat more difficult to install, they provide very secure engagement with the bracket.

FIG. 20 illustrates a further modified bracket for use with spring clips of the present invention. The spring clips of FIGS. 14, 16, 17 and 18 are ideally suited for use with the bracket of FIGS. 20 and 21. In some instances, it is possible to use spring clips of FIGS. 14, 16, 17 and 18 even without the bent-over end portions 85,86 95,96, sufficient retention forces being generated by the rear legs being engaged in the grooves 101,102 of the bracket 100.

FIGS. 22-24 illustrates a further modification of the present invention wherein the spring clip comprises front legs 111,112 and rear legs 113,114 which depend from respective front legs 111,112. The front legs are interconnected by means of a cross member 116. The rear leg 113 is connected to front leg 111 by means of an integral cross member 117 and the rear leg 114 is connected to front leg 112 by means of an integral cross member 118. The spring clip of FIG. 22 mounts on a bracket as illustrated in FIGS. 23 and 24, FIG. 23 being a front view and FIG. 24 being a perspective view. It should be clear that the bent-over portions 115,119 may be omitted and the rear legs inserted through openings, such as opening 51,52 of FIG. 11 or openings 53,54 of FIG. 12. Additionally, side grooves 101,102 may be provided in the bracket 70 of FIGS. 23 and 24, similarly to the bracket of FIGS. 20 and 21. Still further, the bracket 70 of FIGS. 23 and 24 may be provided with a spring clip receiving opening 74 in a side wall thereof for receiving a portion of the spring clip.

With respect to the embodiment of FIGS. 20 and 21, the side walls may be provided with an opening or depression 103,104 for receiving a bent-over portion of a spring clip, such as the bent-over portions 86 illustrated in FIG. 15.

The spring clips of FIGS. 17-19 and FIGS. 22-24 are advantageous in that the cross members extending between the front legs and respective rear legs serve as torsion type spring members which improve the operation of the spring clip. The torsion spring members enable the resulting spring clip to be displaced a greater distance during use, for example to snap an arch wire into the arch wire receiving opening of the bracket without removing the spring clip, without being permanently deformed and while retaining its resiliency and retention force.

Figure 25:
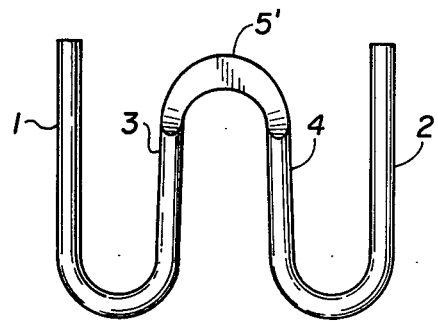
FIG. 25 illustrates a modified embodiment of FIG. 1, on an enlarged scale.

FIG. 25 illustrates a modified embodiment of the spring clip shown in FIG. 1. The connecting portion 5' is thinner than the remaining portion of the spring clip so that when the portion 5' is inserted within a rear opening 12 of a bracket, room is provided for insertion of auxiliaries in said rear opening 12 of the bracket. The thinner portion 5' may be formed by, for example, grinding away a portion of the material at the joining portion 5', or by flattening same with an impact device. In order to provide additional room for auxiliaries, the bracket 10 may be provided with a further groove 19 opening on a wall of the portion of the bracket defining opening 12. See FIG. 4.

Figure 28:
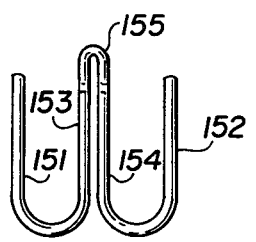
FIGS. 28–30 illustrate a further modified spring clip of the present invention.
Figures 29, 30:
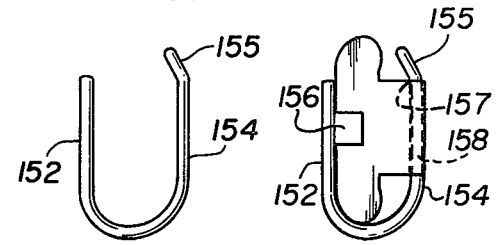

Instead of making connecting portion 5' in FIG. 25 thinner, the portion 5' could be bent in an arc or other curve, for example, as shown by portion 155 in FIGS. 28-30 to provide access for auxiliaries.

Figure 26:
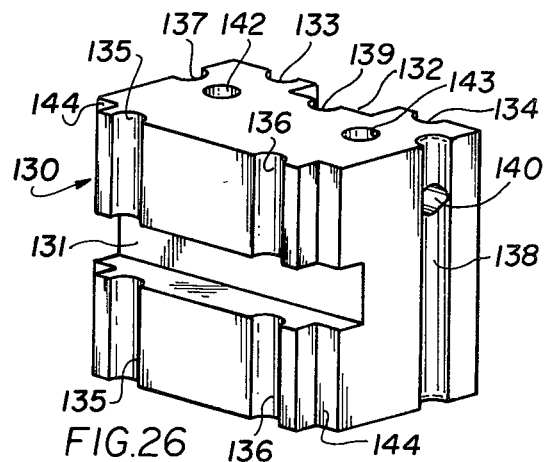
FIGS. 26 and 27 illustrate a novel bracket according to the present invention.

FIG. 26 illustrates a bracket arrangement according to the present invention which is particularly suitable for use with the spring clip of the present invention, but which may also be put to general use, as desired. The bracket 130 is fabricated as a simple block, without conventional tie wings, and comprises an arch wire receiving opening 131, extending horizontally, a rear opening 132, extending vertically, vertical rear grooves 133,134, vertical front grooves 135,136 and vertical side grooves 137,138. Further provided is an additional groove 139 opening into the rear groove 132 which is useful for insertion of auxiliaries, or the like. The rear grooves 133,134 may be used similarly to the grooves 51,52 in FIG. 11. The side grooves 137,138 may be used similarly to the side grooves 101,102 illustrated in FIGS. 21 and 22. The front grooves 135,136 are used similarly to the front grooves 17,18 in FIG. 6. If desired, holes or depressions 140,141 may be provided in the vertical side grooves 137,138 for receiving bent-over portions of a spring clip, or for receiving another type of protruding portion of a spring clip to improve engagement with the bracket. Additionally, or alternatively to grooves 133, 134, through vertical holes 142,143 could be provided so as to serve a similar purpose as holes 53,54 shown in FIG. 12.

Figure 27:
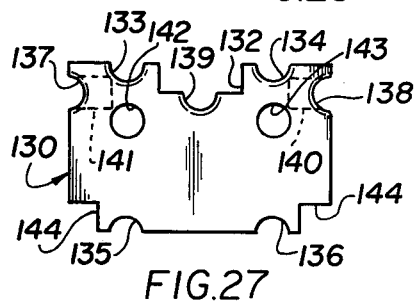

The bracket of FIGS. 26 and 27 may be used with various spring clips described above, and desired. It is a multi-purpose bracket which is simple and economical to construct, and may be made in metal or plastic. For example, the bracket of FIGS. 26 and 27, when made of metal, can be made from an elongated bar, the vertical grooves being formed longitudinally of the bar. The bar may then be cut into separate sections to provide the resultant structure shown in FIGS. 26 and 27. The arch wire receiving opening 131 may be formed either before or after the elongated bar is cut up. The bracket of FIGS. 26 and 27 is also adaptable to being molded from a plastic material. The bracket may also have cut out front corners 144 to receive a front portion of a spring clip to recess same. The corners 144 may be provided alternatively to grooves 135,136 or in addition thereto. The various grooves and cut outs may be rounded or rectangular, as desired.

FIGS. 28-30 illustrate a further spring clip according to the present invention comprising front legs 151,152 which are similar to legs 1 and 2 of FIG. 1, and rear legs 153,154 which are interconnected at 155. The portion 155 is bent inwardly as shown in FIGS. 29 and 30. When mounted on a bracket, as shown in FIGS. 30, the bent-over portion 155 serves as a stop member when the spring clip is pulled downwardly by the dentist so as to provide access to the arch wire receiving opening 156. When the spring clip is pulled downwardly, the bent-over portion 155 abuts against the upper surface 157 of the corner of the bracket defining the rear opening 158 of the bracket. The rear opening 158 is similar to the opening shown in the rear of the bracket 10 in FIG. 4. When the spring clip takes the form of that shown, for example, in FIG. 8, the free ends of the spring clip could be inwardly bent or otherwise deformed so as to serve as stop members during lowering of the spring clip to gain access to the arch wire receiving opening. In this event, the length of the rear legs 33,34 of the embodiment of FIG. 8, for example, is increased so as to provide a sufficient length for movement of the spring clip relative to the bracket to provide access to the arch wire receiving opening. When the downward pulling force is removed, the clip will tend to spring back to its upper or engaged position to retain the arch wire in the arch wire receiving opening of the bracket.

The bending portion 155 in the clip of FIGS. 28-30 also clears the upper end of the clip receiving channel of the bracket so that auxiliaries could be inserted in the channel along with rear legs 163,154 of the spring clip.

Figures 31, 32:
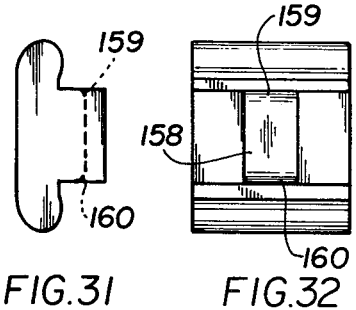
FIGS. 31 and 32 are side and rear views, respectively, of a modified bracket according to the present invention.

In order to facilitate insertion and removal of the spring clip along the lines of FIGS. 28-30 from a bracket, the corners 159,160 of the bracket can be rounded or chamfered, as shown, for example, in FIGS. 31 and 32. In FIG. 32 the bracket is shown in rear view so as to better illustrate the spring clip receiving slot 158 and the chamfered or curved corners. This enhances the tendency of the clip to spring back to its original fully engaged position or the bracket.

The material from which the spring clip is made is of sufficient springiness so that the engaging means, for example the bent-over portion 155 of FIGS. 28-30 can be forced into the rear slot 158 of the bracket and can be removed therefrom upon application of sufficient force. Normally, when lowering the clip relative to the bracket to gain access to the arch wire receiving opening, the forces involved are much less than are required for complete removal of the clip, thereby insuring that the clip will not be inadvertently removed.

Figure 33:
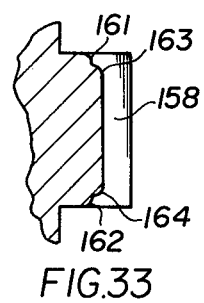
FIG. 33 is a side, partial sectional view, enlarged, of a further modified bracket of the present invention.

In addition to rounding the edges 159,160 as shown in FIG. 31, a step may be provided so as to provide a click-stop warning to the orthodontist that application of further excess force will remove the clip from the bracket. Such an arrangement is shown in FIG. 33, which shows the base part of a typical bracket in enlarged detail. In FIG. 33, the rear slot 158, in addition to having a rounded edge 161,162 at the upper and lower portions thereof, respectively, have respective steps 163,164 formed therein. This provides a sort of click-stop mechanism to further warn the orthodontist that the spring clip is about to be disengaged.

The various spring clips shown in the other embodiments may be similarly modified to provide the engagement mechanism which prevents lowering of the spring clip relative to the bracket to provide access to the arch wire receiving openings. For example, referring to the embodiment of FIG. 10, the legs 43,44 may be extended upwardly and bent-over slightly to provide the effect discussed with respect to the embodiment of FIGS. 28–30. With respect to the embodiment of FIG. 15, the opening 74 may be lengthened to form a slot so as to permit upward and downward movement of the clip relative to the bracket. Likewise, in FIG. 16, a slot may be formed beginning at the upper surface of the base 73 to permit the inwardly bent portions 86 to slide upward and downward relative to the bracket, within limits. The remaining embodiments of the invention can be similarly modified.

The chamfered or rounded edges of the clip receiving channel of the bracket may be provided on different edges so as to cooperate with clips having a corresponding engaging portion. Further, the bracket of FIG. 26 may be provided with such rounded, beveled or chamfered edges.

Figure 34:
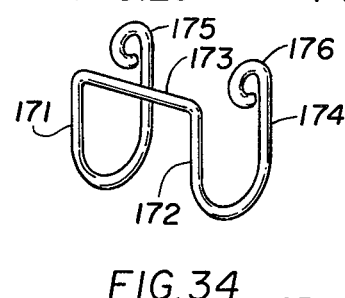
FIG. 34 illustrates a yet further modified spring clip of the present invention.

Referring to FIG. 34, a modified spring clip of the present invention for permitting limited upward and downward movement relative to the bracket, and which is simply and inexpensively manufactured is shown. The ends of the rear legs 173,174 are bent-over on themselves at 175,176. This arrangement provides a bit of resiliency in the free end portions of rear legs 173,174 and serves substantially the same function as the bent-over end portion 155 of FIGS. 28–30. The embodiment of FIG. 34 is useful, for example, in a bracket such as the brackets shown in FIGS. 11 and 12. This bent-over portion 175,176 also serves as springs which cause the clip to tend to spring back to its fully engaged position after the downward force is removed.

Figures 35, 36:
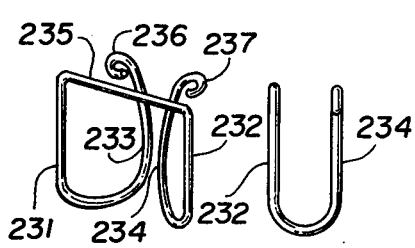
FIGS. 35 and 36 are front perspective and side views of a spring clip of the present invention.

FIGS. 35 and 36, which are front perspective and side views, respectively, illustrate a further spring clip according to the present invention. Generally, the spring clip is configured similar to that of FIG. 8 in that the front legs 231,232 are interconnected by a cross piece 235. The rear legs 233,234 have coiled ends 236,237, respectively, which serve as springs when the spring clip is pulled downwardly relative to a bracket. The spring clip of FIGS. 35 and 36 mount in a bracket similarly to the spring clips shown in FIGS. 3 and 4. During mounting, the spring portions are squeezed in the rear opening of a bracket and when they pass through the opening, they spring outwardly to the position shown in FIG. 35. Upon pulling the spring clip downwardly, the spring portions 236,237 bear on the surfaces of the bracket surrounding the clip receiving opening and tend to springingly unwind as the spring clip is pulled down. When the spring clip is released, the coiled ends 236,237 tend to springingly wind up again and springingly pull the spring clip upward into fully engagement with the bracket.

The surfaces of the bracket with which the clip of FIGS. 35 and 36 is useful are preferably beveled or chamfered around the edges surrounding the clip receiving opening, for example as shown in FIGS. 31, 32 and 33. This further enhances the operation of the coiled portions 236,237 so as to provide the desired spring-type of operation.

As seen in FIG. 35, rear legs 233,234 are preferably gently bent in order to provide further spring action upon downward pulling of the spring clip. As the spring clip is pulled downwardly, the bent legs 233,234 tend to straigthen, thus increasing the spring biassing effect since they will tend to return to their bent condition when the downward pulling force on the clip is released.

Figure 37:
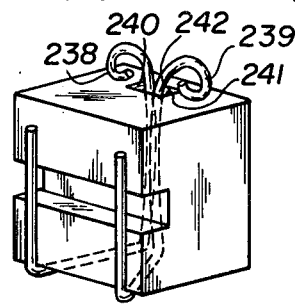
FIG. 37 shows another spring clip of the invention mounted in a bracket.

The embodiment of FIGS. 35 and 36 may be pre-mounted in a bracket so as to provide a bracket and clip assembly. If, during use, the clip of FIG. 35 should break in any way, one of the more easily installed clips of the present invention, for example that shown in FIGS. 1, 2, 8 or 9, could be used to replace the broken spring-biassed clip, if desired. In such a pre-mounted combination, the spring clip may be provided with relatively long spring extensions, as shown in FIG. 37, so as to provide still better spring return action when a downward pulling force on the clip is released. In FIG. 37, a block-type bracket, similar to that of FIG. 26, is shown. In FIG. 37, the side walls 240,241 of the clip receiving opening 242 are chamfered or beveled so as to provide a better cooperating surface for the spring ends 238,239 of the spring clip. The spring clip is fabricated of springy wire such that it tends to return to its original position when a downward pulling force is released. If the spring clip of FIG. 37 breaks, it may be removed and replaced with another type of spring clip previously described which is more easily inserted into the spring clip receiving opening 242. While the spring clip receiving opening 242 is shown as a rectangular bore in the bracket, it could take other forms, such as a circular bore or an open channel opening to the rear surface of the bracket. Other configurations could equally well be used.

Figure 38:
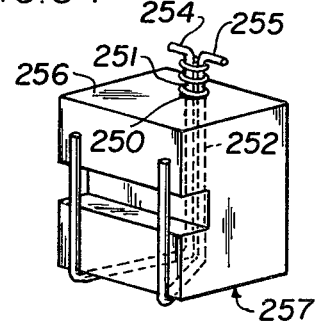
FIG. 38 shows another spring biassed clip of the invention in combination with a bracket.

FIG. 38 illustrates a further modification of the present invention wherein the rear legs 251,252 of a spring clip pass through a bore 250 in a bracket 257. A coil spring 253 is mounted around the ends of the legs 251,252 and the free ends 254,255 of the legs are either bent-over or otherwise deformed to retain the spring 253 on the rear legs 251,252. The bore 250 is of small enough diameter so that the spring 253 does not pass through and bears against the upper surface 256 of the bracket 257. If it is desired that the spring 253 not protrude above the upper surface 256 of the bracket 257, the bore 250 may have a larger diameter end portion so that the spring 253 and the free ends of the legs 251,252 can be recessed within the body of bracket 257. If the spring or free ends 254,255 should break or otherwise become inoperative during use, the complete spring clip may be removed and replaced with another type of spring clip of the present invention, previously described, which is more easily inserted into the spring receiving bore 250. Preferably, the arrangement of FIG. 38 is pre-assembled at manufacture and is sold as a complete unit ready for installation in the mouth.

The embodiment of FIGS. 20 and 21 may be modified to round or bevel the upper portions of side grooves, 101,102 and the rear legs of the spring clip may have spring-type means for resiliently engaging same, for example similar to those shown in FIG. 34, but the loops 175,176 being directed inwardly toward the rounded or beveled edge. Similarly, the upper ends of the side grooves 137,138 of FIG. 26 may be beveled or rounded as shown in FIG. 26 to provide similar effects.

Figures 39A, 39B:
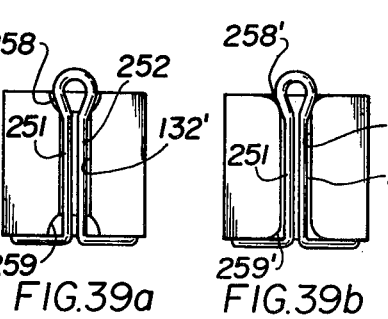
FIGS. 39a and 39b are rear views of further modified spring clips and brackets of the present invention.

FIGS. 39a and 39b are rear views of brackets, for example similar to the bracket of FIG. 26, wherein the rear opening 132' has chamfered or otherwise cut-out entry surfaces. In FIG. 39a, the cut-out upper and lower entry surfaces 258,259 are shown concave, whereas in FIG. 39b the entry surfaces 258' and 259' are shown convex. In these embodiments, the rear legs 251,252 are either forced into the bracket opening 132' after the bracket is mounted on a tooth, or the spring clip is pre-assembled with the rear legs already in the bracket opening 132' prior to mounting same on a tooth. The beveled or cut-out surfaces 258,259, 258',259' serve as camming surfaces so that when the spring clip is pulled downwardly, the loop at the upper portion of the rear legs will springingly flex in order to tend to cause the spring clip to return upward to its original position after the downward pulling force is released from the spring clip.

Figure 40:
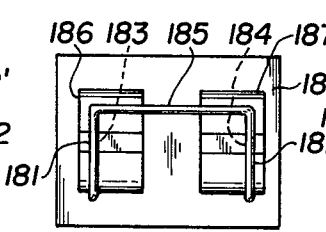
FIGS. 40 and 41 show front and top views of a spring clip of the present invention utilized with a twin bracket arrangement.
Figure 41:
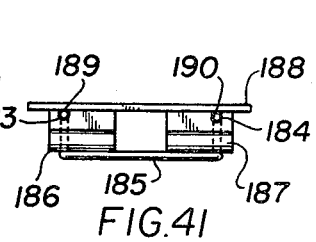

Referring to FIGS. 40 and 41, which show front and top views of a spring clip used with a twin bracket, the spring clip comprises front leg members 181,182 connected with rear leg members 183,184, the free ends of the front leg members 181,182 being interconnected by a cross member 185. The spring clip generally takes the shape of that shown in FIG. 10, but the cross member 185 is extended so that the spring clip spans a twin bracket arrangement 186,187. The brackets 186,187 may be mounted on a plate 188, or the like, or may be directly mounted to a tooth. As seen in FIG. 41, the rear legs 183,184 extend upwardly through openings 189,190 in the respective brackets 186,187. The openings may be made as shown in FIG. 41, may be through bores extending through the brackets as shown in FIG. 12, or may have additional auxiliary receiving openings as shown, for example, in FIGS. 4, 26 and 27. The front legs 181,182 may have cut-out or bent-out portions similar to portions 26,27; 26',27' shown in FIGS. 7a and 7b for engaging an arch wire. The fronts of the brackets 186,187 may have grooves for at least partially receiving the spring clip, such as shown in FIG. 6.

The spring clip shown in FIGS. 40 and 41 is exemplary only. The rear legs of the spring clip of FIGS. 40 and 41 may take the shape as shown in FIGS. 14–16 so as to engage either surfaces of the bracket or bores or depressions therein. The spring clip for a twin bracket arrangement may also have crossed over portions, such as shown in FIGS. 17–19 and 22–24.

Figure 42:
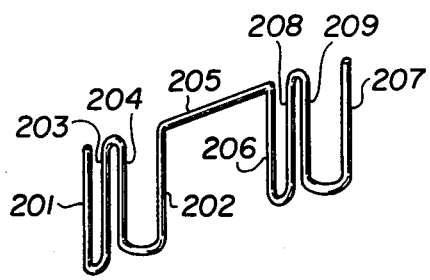
FIG. 42 illustrates another spring clip of the present invention useful with twin bracket arrangements.

FIG. 42 illustrates a modified spring clip arrangement for use with a twin bracket such as shown in FIGS. 40 and 41. The spring clip of FIG. 42 is useful with a bracket having a rear opening 14 therein, such as the brackets of FIGS. 4 and 6. The spring clip shown in FIG. 42 essentially comprises two spring clips similar to that of FIG. 1, interconnected by a cross member 205. Particularly, the portion 201–204 and the portion 206–209 each operates as the spring clip of FIGS. 1–4, but they are interconnected by cross member 205. The spring clip of FIG. 42 is fabricated of a single wire member, preferably of springy material. This arrangement provides more secure retention of an arch wire, or the like, in the arch wire receiving openings of the twin bracket arrangement. This is because the arch wire is retained at two points on each bracket of the twin bracket arrangement when using the spring clip of FIG. 42. The portion 205 spans the space between the two brackets of the twin bracket arrangement.

While the twin bracket arrangement of FIGS. 40 and 41 is shown in accordance with conventional brackets, the wingless brackets, for example shown in FIGS. 26 and 27 could be used, as well as other brackets not specifically described.

Figure 43:
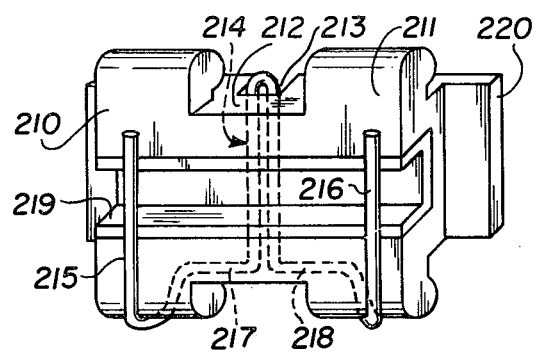
FIG. 43 illustrates another twin bracket arrangement and a spring clip of the present invention mounted thereon.

FIG. 43 illustrates a further twin bracket arrangement utilizing a spring clip of the present invention. The twin bracket arrangement comprises two adjacent brackets 210,211 and a member 212 interconnecting the brackets. The member 212 has a slot or opening 213 therein for receiving the rear portion 214 of an orthodontic spring clip of the present invention. The front portions 215,216 of the spring clip extend around the front surfaces of the brackets, as shown in FIG. 43, to retain an arch wire in the arch wire receiving openings of the brackets. In this arrangement, the rear portion and the front legs are interconnected by means of, for example, transverse portions 217,218 which act to offset the front and rear leg portions and further serve as torsion springs to facilitate springing of the front legs 215,216 away from the arch wire receiving opening to permit insertion of an arch wire in the openings. The opening 213 is shown as a channel—other arrangements, such as through bores, could be used. The bracket 210 is shown having a hard liner 219 in the arch wire receiving opening, such as that shown and described in my copending U.S. patent application Ser. No. 782,028. Also, a mounting flange 220 is provided.

Figure 44:
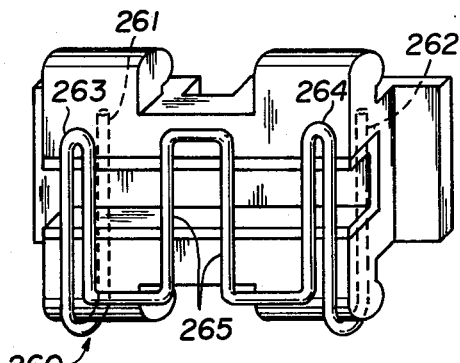
FIGS. 44–47 illustrate further spring clips for use with a twin bracket arrangement.

FIG. 44 illustrates another twin bracket arrangement with an orthodontic spring clip 260 installed thereon. The spring clip 260 is formed of a single piece of wire of appropriate springiness and has rear legs 261,262 which pass through bores or openings (not shown) in the rear portion of the bracket arrangement. The front legs 263,264 are interconnected by a further front leg 265 which passes over the arch wire receiving opening of the bracket so as to provide still better retention of an arch wire therein.

Figure 45:
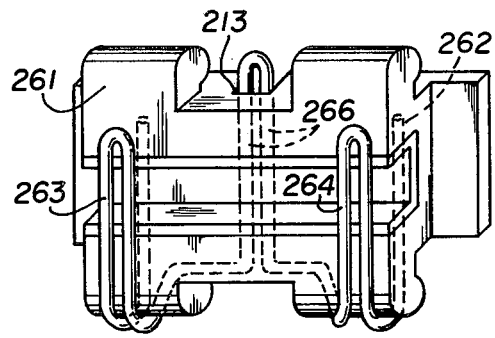

FIG. 45 illustrates a spring clip similar to that of FIG. 44, except wherein the rear leg 266 passes through a rear bore or opening 213 in the bracket. In this arrangement, only front legs 263,264 retain the arch wire in the arch wire receiving opening of the bracket. In the arrangement of FIG. 45, the length of the rear leg 266 is preferably greater than the length of the other rear legs 261,262 so that the middle rear leg 266 can serve as a centering member to facilitate alignment and insertion of the other rear legs 261,262 in the rear bracket openings.

Figure 46:
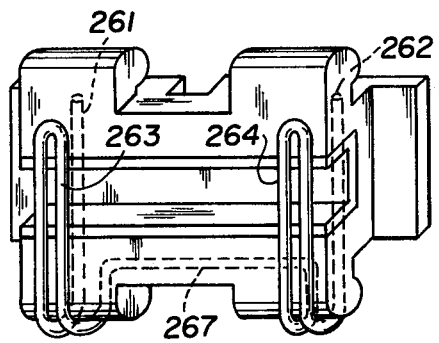

FIG. 46 illustrates a further embodiment of a spring clip according to the present invention wherein the middle portion 267 which interconnects the front legs 263,264 runs behind the bracket.

Figure 47:
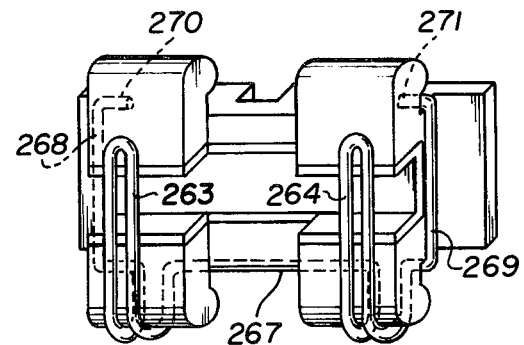

FIG. 47 illustrates a further spring clip for use with a twin bracket arrangement wherein the rear legs 268,269 have bent-over portions 270,271, respectively for engaging over a surface of the twin bracket arrangement. The rear legs 268,269 are adapted to run along a side surface, toward the rear, of the twin bracket arrangement so as to mount the spring clip to the bracket in a manner similar to that described in connection with, for example, FIG. 16. Engaging openings may be provided in the side surfaces of the twin bracket of FIG. 47, similar to those of FIG. 15, to engage portions of the spring clip.

In the twin bracket embodiments described above, it should be clear that grooves or the like may be provided in the surfaces, particularly the front surfaces, of the bracket so as to at least partially recess the spring clips therein. Additionally, in the arrangement of FIG. 47, a side groove, for example as shown in FIGS. 20 and 21, may be provided. Various modifications may be made to the spring clips of the twin bracket arrangement within the inventive concept.

The spring clips of the present invention are preferably fabricated of relatively thin wire, for example 0.011 diameter round wire. Other diameters of round wire, or other sizes and shapes of wires could also be used, depending upon the particular application. As described herein, the wire from which the spring clips are fabricated is preferably of a springy nature so that the wire may be pulled or flexed from its original position, and then spring back to its original shape and position.

Figure 48:
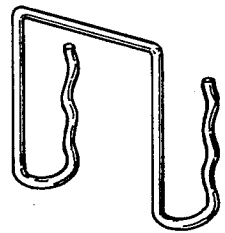
FIG. 48 shows still another embodiment of a spring clip of the present invention.

As shown in FIG. 48, the rear legs of the spring clips of the present invention may be wavy, arcuately formed, or otherwise shaped so as to better wedge inside a spring clip receiving opening of a bracket. Since the spring clip is preferably fabricated of a springy wire, the peak-to-peak distance between the oppositely directed undulations of the rear legs is preferably slightly greater than the size of the oening within which it is to be placed, whereby when the spring clip is forced into the clip receiving opening of a bracket, the opposed undulations will spring towards each other so as to tightly wedge the spring clip in the bracket. Any of the arrangements of the present invention hereinbefore described may be provided with such additional engaging means so as to enhance the retainment of the spring clip by the bracket.

FIG. 49 illustrates an embodiment of the invention used in a round bracket 280 having an arch wire receiving opening 281 therein. FIG. 50 is a sideview of the bracket. The bracket has spring clip engaging cut-outs or slots 282, 283 in the rear portion 284 thereof. The spring clip comprises legs 285, 286, each having bent-in or otherwise deformed portions 287, 288 respectively. Portions 287, 288 engage in the cut-outs or depressions 282, 283, respectively. The legs 285, 286 are preferably curved to conform to the contour of the rear portion 284 of the bracket. To lower the spring clip below the arch wire receiving opening for insertion of an arch wire therein, the spring clip is merely pulled down and the portions 287, 288 move downward in cut-outs 282, 283 to permit downward movement of the spring clip. The curved legs 285, 286, acting against the curved surfaces of the rear portion 284 of the bracket, tend to retain the spring clip in its upward position, and tend to spring the clip upward after it is pulled down. Cut-outs 282, 283 may take the form of depressions, grooves, or other equivalent structural arrangements.

FIG. 51 illustrates a bracket 290 having depressions 291, 292 in the rear portion thereof. The spring clip comprises rear legs 293, 294, each of which has respective bent-in or deformed portions 295, 296 which are engagingly received in depressions or cut-outs 291, 292. The legs 293, 294 are outwardly bulged (shown exaggerated in FIG. 51). When the front portion of the spring clip is pulled downwardly to expose the arch wire receiving opening, the side legs 293, 294 are straightened against their spring force to permit downward movement of the front portion 297 of the spring clip. Due to the springiness of the wire, the rear portions 293, 294 will tend to return to their original bowed condition, thus urging the front portion 297 upward upon release of the downward pulling force so as to again cover the arch wire receiving opening shown in FIG. 51.

The brackets of FIGS. 49, 50 and 51 may be provided with cut-outs or depressions 300, 301 in the outer lip portion thereof so as to positively engage the portions of the spring clip which are bent around the face or outer portion of the bracket.

In the embodiment of FIG. 49, the spring clip may take the form as that shown in FIGS. 17 or 22, the rear leg portions being curved or arched so as to generally conform to the curve of the round bracket.

FIGS. 53 and 54 are respective front and top views of a further modified round bracket of the present invention. The bracket 310 comprises an arch wire receiving opening 311 and a vertical opening 312 for receiving a spring clip therein. The rear or base portion 313 of the bracket has a further elongated bore or channel 314 formed therein, the bore or channel extending the complete height of the rear portion 313 and terminating the flattened portion 315 of the rear portion 314. FIG. 55 illustrates a spring clip 320 which is suitable for use with the bracket of FIGS. 53 and 54. The spring clip 320 is pre-assembled to the bracket during manufacture. FIG. 56 shows the spring clip of FIG. 55 mounted in a bracket of FIG. 53. The front leg 321 of the spring clip 320 fits within the outer vertical channel 312 of the bracket and the rear leg 322 is inserted in the rear bore 314 of the bracket. The bent-over portion 323 of the rear leg is provided so as to retain the spring clip in the bracket when the spring clip is pulled downwardly so as to expose the arch wire opening 311. The tortuously bent portion 324 is behind the front face of the bracket and maintains the spring clip in proper orientation with the bracket even when the spring clip is pulled downwardly. The downward movement of the spring clip is limited by the bent-over portion 323 abutting against the flattened upper surface 315 of the bracket.

FIG. 57 illustrates a spring clip 330 identical to that of FIG. 55 except that the bent-over portion 333 is elongated so that the end portion 334 of the bent-over portion abuts against a surface of the rear portion 313 of the bracket. Upon downward pulling of the spring clip, the portion 333 will continue to bear against the rear portion 313 of the bracket so as to permit resilient downward movement of the spring clip relative to the bracket. The resiliency of the portion 333 will urge the spring clip back in the upper direction when the downward pulling force is released.

FIGS. 58 and 59 illustrate respective modifications of the embodiments of FIGS. 57 and 55. In the embodiment of FIGS. 58 and 59, the loop portions 330' and 321' are provided so as to provide a torsion bending effect, for example as a reaction to forces urging an arch wire out of engagement with the arch wire receiving channel of a bracket. The torsion bending characteristics have been found to provide excellent forces which retain the arch wire in the arch wire receiving slot of a bracket. This arrangement also provides two contact points at which the arch wire is retained relative to the channel.

Figure 60:
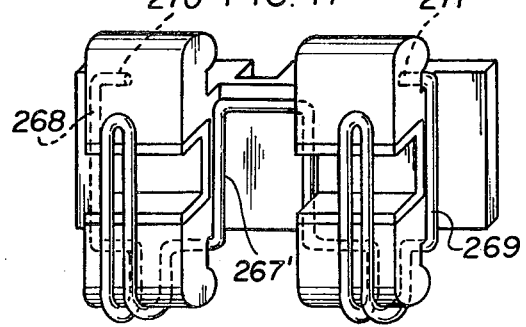
FIG. 60 is a modification of the arrangement of FIG. 47.

FIG. 60 illustrates an arrangement whereby portion 267' is provided so as to pass between the respective brackets of the twin bracket arrangement. This adds additional strength to the overall structure and prevents the spring clip from moving in the axial direction of the arch wire. By virtue of the portion 267' being retained behind an arch wire, and the forward portions 263 and 264 extending infront of the arch wire, excellent torsion bending effects are obtained in the horizontal portions interconnecting the portions 263 and 264 with the central member 267'.

As should be apparent from the foregoing descriptions of the preferred embodiments of the invention, in a preferred arrangement the spring clip utilizes two legs which are offset in the axial direction of the arch wire so as to provide torsion bending effects between the relative portions of the spring clip, thereby enhancing reliability, improving retention forces on the arch wire and reducing the possibility that bending forces on the spring clip will cause permanent deformation thereof. Some of the embodiments of the invention illustrate the torsion-bending effect to a greater degree than others. The choice of the particular spring clip depends upon the application and the type of bracket with which it is to be used.

When using the Nitinol wire, for example the type of wire disclosed in U.S. Pat. No. 4,037,324, the application of heat can be advantageously used so as to form the orthodontic spring clip to its desired positions in the mouth. The application of heat may be indirect, for example by blowing hot air on the wire clip after it is in the mouth. Such a heating operation may faciliate use of the spring clip and it is believed that heating may also be used to re-shape the spring clip in the mouth so as to restore any retention forces which it may have lost during periods of use.

It should be clear that the various brackets shown throughout the drawings could be fabricated from either metal or plastic material. Also, the various modifications of the brackets may be used in any combination, as desired, depending upon intended use. Also, the spring clips shown in the drawings can be modified, various features from different embodiments being combined, as desired, to provide specific characteristics. In use, when a spring clip of the present invention is already mounted on a bracket, it is possible, due to the resilience of the spring clip, for the spring clip to be sprung away from the front surface of the bracket on which it is mounted, and the arch wire snapped between the spring clip and the bracket so as to be received into the arch wire receiving opening of the bracket. The front legs of the spring clip may be sprung away from the bracket front face either under the influence of the arch wire alone, or by means of another implement, such as a pair of pliers, or the like. Due to the fact that the spring clips of the present invention have two spaced legs on the front surfaces thereof, it is possible to impart rotation forces to a tooth under the influence of an arch wire in the arch wire receiving opening of the bracket. Since the spring clip is fabricated preferably of wire, it is inexpensive to manufacture and of substantially universal use. When used with plastic brackets, the wire spring clip of the present invention is generally unobtrusive in the mouth and does not substantially degrade the esthetic appearance of the orthodontic assembly in the mouth. The various features of the invention may be combined in any desired combination, depending upon the desired resultant effects.

I claim:

1. An orthodontic spring clip made of bent wire for use with an orthodontic bracket means having an elongated arch wire receiving opening formed in a front surface portion thereof, the wire spring clip comprising:
    a first resilient wire portion comprising at least two spaced apart elongated members for engaging and passing over at least a part of said front surface portion of the bracket having said arch wire receiving opening therein, and for passing over at least a portion of said arch wire receiving opening to retain an arch wire relative to said bracket, said at least two elongated members being spaced apart a distance so as to pass over a part of said front surface portion of the bracket and over at least a portion of said arch wire receiving opening intermediate the ends of said elongated arch wire receiving opening;
    a second wire portion comprised of at least two elongated members coupled to said first wire portion of said clip for engaging a portion of said bracket remote from said front surface of said bracket when said first wire portion of said clip at least partially covers said arch wire receiving opening of the bracket, said elongated members of said second wire portion of said clip crossing each other; and
    means coupling together the elongated members of at least one of said first and second clip portions.

2. An orthodontic clip according to claim 1, wherein said at least two elongated members of said second portion are spaced apart from each other.

3. An orthodontic clip according to claim 2, wherein said two spaced apart elongated members of said second portion are respectively integral with and extend from said at least two spaced apart elongated members of said first portion.

4. An orthodontic clip according to claim 3, wherein said coupling means comprises a transverse wire portion interconnecting the ends of said elongated members of said first portion remote from said second portion.

5. A orthodontic clip according to claim 3, wherein said clip is fabricated of a metal spring wire member which integrally forms said first and second portions.

6. An orthodontic clip according to claim 1, wherein said clip is fabricated of a single metal spring wire member which integrally forms said first and second portions.

7. An orthodontic clip according to claim 6, wherein said metal wire is an amorphous spring wire.

8. An orthodontic clip according to claim 1, wherein each of said elongated members of said first portion has at least one contoured portion along the length thereof for at least partially engaging an arch wire, or the like.

9. An orthodontic clip according to claim 8, wherein said first and second elongated members of said first portion each have a plurality of contoured portions along the length thereof for engaging an arch wire, or the like in selected contoured portions.

10. An orthodontic clip according to claim 3, wherein said spaced apart elongated members of said second portion are resiliently interconnected by said coupling means so as to be resiliently displaceable toward each other.

11. An orthodontic clip according to claim 1, wherein said elongated members of said second portion are spaced a predetermined distance apart and are resiliently interconnected by said coupling means so as to be resiliently displaceable toward each other.

12. An orthodontic clip according to claim 1, wherein said elongated members of said second portion comprise bracket engaging means.

13. An orthodontic clip according to claim 12, wherein said bracket engaging means comprises protruding end portions of said elongated members of said second portion.

14. An orthodontic clip according to claim 13, wherein said elongated members of said first and second portions are respectively integrally connected with each other and wherein said coupling means interconnects said elongated members of said first portion at the ends thereof remote from said elongated members of said second portion, the ends of said elongated members of said second portion remote from said first portion comprising bent-over bracket engaging means.

15. An orthodontic clip according to claim 1, wherein respective elongated members of said first and second portions are integrally connected together, and each pair of integrally connected elongated members generally defines a U-shape.

16. An orthodontic clip according to claim 1, wherein said elongated members of said second portion cross each other in a generally X-shaped configuration rearwardly of the portion thereof which is adapted to engage a front surface of an orthodontic bracket.

17. An orthodontic clip according to claim 1, wherein said crossing over portions of said elongated members of said second portion define torsion springs.

18. An orthodontic clip according to claim 1, wherein said elongated members of said second wire portion comprise bracket engaging means in the vicinity of the ends thereof remote from said crossing over portion.

19. An orthodontic clip according to claim 18, wherein said coupling means comprises means interconnecting said elongated members of said first portion.

20. An orthodontic clip according to claim 19, wherein said clip is made of a single integral metal wire.

21. An orthodontic clip according to claim 1, wherein said coupling means comprises means interconnecting said elongated members of said second portion together by means of an interconnecting portion which has a smaller cross-sectional dimension than said elongated members and is adapted to be inserted in a clip receiving opening of a bracket, said smaller cross-sectional dimension permitting mounting of auxiliaries in said clip receiving opening of said bracket.

22. An orthodontic clip according to claim 1, wherein said elongated members of said second portion are adapted to both be received in an elongated clip receiving opening of a bracket.

23. An orthodontic clip according to claim 1, wherein said elongated members of said second portion comprises respective means for passing through respective clip receiving openings of a bracket.

24. An orthodontic clip according to claim 1, wherein said elongated members of said first portion of said clip are adapted to be at least partially received in respective grooves on a front surface of a bracket.

25. An orthodontic clip according to claim 24, wherein said elongated members of said second portion of said clip are adapted to be at least partially received in respective grooves on opposing side surfaces of a bracket.

26. An orthodontic clip according to claim 1, wherein said elongated members of said second portion of said clip are adapted to be at least partially received in respective grooves on opposing side surfaces of a bracket.

27. An orthodontic clip according to claim 26, wherein said elongated members of said second portion comprise bracket engaging means which are engageable with further clip engaging means of a bracket, the further clip engaging means of the bracket being in communication with the grooves on the side surfaces thereof.

28. An orthodontic assembly according to claim 1, wherein said elongated members of said second portion comprise bracket engaging means.

29. An orthodontic assembly according to claim 28, wherein said bracket engaging means comprises an undulating surface portion of said elongated members of said second clip portion for being wedged in said clip receiving means of said bracket.

30. An orthodontic clip according to claim 1, wherein said coupling means comprises means for permitting an auxiliary to be received in said opening.

31. An orthodontic clip according to claim 30, wherein said coupling means comprises a bent-back portion.

32. An orthodontic spring clip according to claim 1, wherein said wire is a near-stoichiometric alloy of nickel and titanium.

33. An orthodontic clip according to claim 32, wherein the composition of said alloy is about $TiNi_{0.935}CO_{0.065}$.

34. An orthodontic spring clip according to claim 1, wherein at least two of said elongated members of said first and second wire portions are spaced from each other in the axial direction of the arch wire so as to exhibit torsional bending forces therebetween.

35. An orthodontic clip according to claim 1, wherein said at least two spaced apart elongated members of said first wire portion pass completely over said arch wire receiving opening of the bracket.

36. An orthodontic clip according to claim 1, wherein said second wire portion engages said bracket intermediate the ends of said elongated arch wire receiving opening.

37. An orthodontic assembly comprising: an orthodontic bracket means having an elongated arch wire receiving opening in a front surface portion thereof, and clip receiving means; and
an orthodontic clip including:
a first resilient wire portion comprising at least two spaced apart elongated members for engaging and passing over at least a part of said front surface portion of said bracket and for passing over at least a portion of said arch wire receiving opening to retain an arch wire relative to said bracket, said at least two elongated members being spaced apart a distance so as to pass over a part of said front surface portion of said bracket and over at least a portion of said arch wire receiving opening intermediate the ends of said elongated arch wire receiving opening;
a second wire portion comprised of at least two elongated members coupled to said first wire portion of said clip and including means for engaging said clip receiving means of said bracket remote from said front surface of said bracket when said first wire portion of said clip at least partially covers said arch wire receiving opening of said bracket, said elongated members of said second wire portion of said clip crossing each other; and
means coupling together the elongated members of at least one of said first and second clip portions.

38. An orthodontic assembly according to claim 37, wherein said at least two elongated members of said second portion are spaced apart from each other.

39. An orthodontic assembly according to claim 38, wherein said two spaced apart elongated members of said second portion are respectively integral with and extend from said at least two spaced apart elongated members of said first portion.

40. An orthodontic assembly according to claim 39, wherein said coupling means comprises a transverse wire portion interconnecting the ends of said elongated members of said first portion remote from said second portion.

41. An orthodontic assembly according to claim 39, wherein said clip is fabricated of a metal spring wire member which integrally forms said first and second portions.

42. An orthodontic assembly according to claim 37, wherein said clip is fabricated of a single metal spring wire member which integrally forms said first and second portions.

43. An orthodontic assembly according to claim 42, wherein said metal wire is an amorphous spring wire.

44. An orthodontic assembly according to claim 37, wherein each of said elongated members of said first portion has at least one contoured portion along the length thereof for at least partially engaging an arch wire, or the like.

45. An orthodontic assembly according to claim 44, wherein said first and second elongated members of said first portion each have a plurality of contoured portions along the length thereof for engaging an arch wire, or the like in selected contoured portions.

46. An orthodontic assembly according to claim 31, wherein said spaced apart elongated members of said second portion are resiliently interconnected by said coupling means so as to be resiliently displaceable toward each other.

47. An orthodontic assembly according to claim 37, wherein said spaced elongated members of said second portion are resiliently interconnected by said coupling means so as to be resiliently displaceable toward each other.

48. An orthodontic assembly according to claim 37, wherein said elongated members of said second portion comprise bracket engaging means.

49. An orthodontic assembly according to claim 48, wherein said bracket engaging means comprises protruding end portions of said elongated members of said second portion.

50. An orthodontic assembly according to claim 49, wherein said bracket comprises means for engagingly receiving said protruding end portions of said elongated members of said second portion.

51. An orthodontic assembly according to claim 50, wherein said receiving means of said bracket comprises an opening in a side wall of said bracket for receiving and engaging said protruding end portions.

52. An orthodontic assembly according to claim 50, wherein said bracket comprises respective grooves on opposite side portions thereof for receiving and engaging said elongated members of said second portion.

53. An orthodontic assembly according to claim 52, wherein said receiving and engaging means of said bracket comprises at least a depression in each of said grooves on said opposing sides of said bracket.

54. An orthodontic assembly according to claim 49, wherein said elongated members of said first and second portions are respectively integrally connected with each other and wherein said coupling means interconnects said elongated members of said first portion at the ends thereof remote from said elongated members of said second portion, the ends of said elongated members of said second portion remote from said first portion comprising bent-over bracket engaging means.

55. An orthodontic assembly according to claim 37, wherein respective elongated members of said first and second portions are integrally connected together, and each pair of integrally connected elongated members generally defines a U-shape.

56. An orthodontic assembly according to claim 37, wherein said elongated members of said second portion cross each other in a generally X-shaped configuration rearwardly of the portion thereof which is adapted to engage a front surface of an orthodontic bracket.

57. An orthodontic assembly according to claim 37, wherein said crossing over portions of said elongated members of said second portion define torsion springs.

58. An orthodontic assembly according to claim 37, wherein said elongated members of said rear portion comprise bracket engaging means in the vicinity of the ends thereof remote from said crossing over portion.

59. An orthodontic assembly according to claim 58, wherein said coupling means comprises means interconnecting said elongated members of said first portion.

60. An orthodontic assembly according to claim 59, wherein said clip is made of a single integral metal wire.

61. An orthodontic assembly according to claim 37, wherein said bracket has a clip receiving opening therein, and said coupling means comprises means interconnecting said elongated members of said second portion together by means of an interconnecting portion which has a smaller cross-sectional dimension than said elongated members so as to permit mounting of auxiliaries in said clip receiving means of said bracket.

62. An orthodontic assembly according to claim 37, wherein said bracket includes an elongated clip receiving opening, said elongated members of said second portion being adapted to both be received in said elongated clip receiving opening.

63. An orthodontic assembly according to claim 37, wherein said bracket includes at least two clip receiving openings, said elongated members of said second portion comprising respective means for passing through respective clip receiving openings of said bracket.

64. An orthodontic assembly according to claim 37, wherein said bracket comprises respective grooves on a front surface thereof for at least partially receiving respective elongated members of said first portion of said clip.

65. An orthodontic assembly according to claim 64, wherein said bracket comprises respective grooves on surfaces thereof for engagingly receiving respective elongated members of said second portion.

66. An orthodontic assembly according to claim 37, wherein said bracket comprises respective grooves on surfaces thereof for engagingly receiving respective elongated members of said second portion.

67. An orthodontic assembly according to claim 66, comprising further clip engaging means in communication with said grooves which receive said elongated members of said second portion, said elongated members of said second portion comprising bracket engaging means which are engageable with said further clip engaging means of said bracket.

68. An orthodontic assembly according to claim 37, wherein said elongated members of said second portion comprise bracket engaging means.

69. An orthodontic assembly according to claim 68, wherein said bracket engaging means comprises an undulating surface portion of said elongated members of said second clip portion for being wedged in said clip receiving means of said bracket.

70. An orthodontic clip according to claim 37, wherein said coupling means comprises means for permitting an auxiliary to be received in said opening.

71. An orthodontic clip according to claim 70, wherein said coupling means comprises a bent-back portion.

72. An orthodontic spring clip according to claim 37, wherein said wire is a near-stoichiometric alloy of nickel and titanium.

73. An orthodontic clip according to claim 72, wherein the composition of said alloy is about $TiNi_{0.935}CO_{0.065}$.

74. An orthodontic spring clip according to claim 37, wherein at least two of said elongated members of said first and second wire portions are spaced from each other in the axial direction of the arch wire so as to exhibit torsional bending forces therebetween.

75. An orthodontic clip according to claim 37, wherein said at least two spaced apart elongated members of said first wire portion pass completely over said arch wire receiving opening of the bracket.

76. An orthodontic clip according to claim 37, wherein said second wire portion engages said bracket intermediate the ends of said elongated arch wire receiving opening.

77. An orthodontic assembly comprising:
a twin orthodontic bracket means comprising a pair of adjacent brackets and clip receiving means, each bracket having an elongated arch wire receiving opening in a front surface portion thereof; and
an orthodontic clip including:
a first wire portion comprising at least two spaced apart elongated members, at least one of said elongated members engaging and passing over at least a part of said front surface portion of one of said brackets of said twin bracket and passing over at least a portion of said arch wire receiving opening of said one of said brackets, and at least another one of said elongated members engaging passing over at least a part of said front surface portion of the other of said brackets of said twin bracket and passing over at least a portion of said arch wire receiving opening of said other bracket of said twin brackets to retain an arch wire relative to said twin bracket, said at least two elongated members being spaced apart a distance so as to pass over a part of said front surface portions of said brackets and over at least a portion of said arch wire receiving openings intermediate the ends of said elongated arch wire receiving openings;
a second wire portion comprised of at least two elongated members coupled to said first wire portion of said clip and including means for engaging said clip receiving means of said twin bracket with said first portion of said clip at least partially covering said arch wire receiving openings of said brackets; and
means coupling together the elongated members of at least one of said first and second clip portions.

78. An orthodontic assembly according to claim 77, wherein said first portion of said clip includes at least four spaced apart elongated members, two of said elongated members of said first portion passing over at least a portion of the arch wire receiving opening of one bracket of said twin bracket and another two of said elongated members passing over at least a portion of the arch wire receiving opening of the other bracket of said twin brackets.

79. An orthodontic assembly according to claim 78, wherein said first portion of said clip further comprises means extending over said at least a portion of said arch wire receiving opening of said twin bracket and being located intermediate said at least two elongated members of said first portion.

80. An orthodontic assembly according to claim 79, wherein said first portion of said clip further comprises means extending over at least a portion of said arch wire receiving opening of said twin bracket and being located intermediate said at least two elongated members of said first portion.

81. An orthodontic assembly according to claim 77, wherein said clip receiving means of said twin bracket which is located intermediate said two brackets of said twin brackets and said at least two elongated members of said second portion are adapted to be received by said clip receiving means.

82. An orthodontic assembly according to claim 77, wherein said clip is fabricated of a single metal wire member which integrally forms said first and second portions.

83. An orthodontic assembly according to claim 82, wherein said metal wire is an amorphous spring wire.

84. An orthodontic assembly according to claim 77, wherein each of said brackets of said twin bracket means comprises a clip receiving means, and said at least two elongated members of said second portion are adapted to be received by respective clip receiving means of said respective brackets.

85. An orthodontic spring clip made of bent wire for use with a twin orthodontic bracket means having a pair of adjacent brackets and clip receiving means, each bracket having an arch wire receiving opening in a front surface portion thereof, the wire spring clip comprising:
a first wire portion comprising at least two spaced apart elongated members, at least one of said elongated members engaging and passing over at least a part of said front surface portion of each respective bracket, and passing over at least a portion of said arch wire receiving opening of each respective bracket to retain an arch wire relative to said twin bracket, said at least two elongated members being spaced apart a distance so as to pass over a part of said front surface portion of each of said brackets and over at least a portion of each of said arch wire receiving openings intermediate the ends of said elongated arch wire receiving openings;
a second-wire portion comprised of at least two elongated members coupled to said first wire portion of said clip for engaging said clip receiving means of said twin bracket when said first wire portion of said clip at least partially covers said arch wire receiving openings; and
means coupling together the elongated members of at least one of said first and second clip portions.

86. An orthodontic assembly according to claim 85, wherein said first portion of said clip includes at least four spaced apart elongated members, two of said elongated members of said first portion passing over at least a portion of the arch wire receiving opening of one bracket of said twin bracket and another two of said elongated members passing over at least a portion of the arch wire receiving opening of the other bracket of said twin brackets.

87. An orthodontic assembly according to claim 85, wherein said first portion of said clip further comprises means extending over at least a portion of said arch wire receiving opening of said twin bracket and being located intermediate said at least two elongated members of said first portion.

88. An orthodontic assembly according to claim 85, wherein said first portion of said clip further comprises means extending over at least a portion of said arch wire receiving opening of said twin bracket and being located intermediate said at least two elongated members of said first portion.

89. An orthodontic assembly according to claim 85, wherein said clip receiving means of said twin bracket is located intermediate said two brackets of said twin brackets and said at least two elongated members of said second portion are adapted to be received by said clip receiving means.

90. An orthodontic assembly according to claim 85, wherein each of said brackets of said twin bracket means comprises a clip receiving means, and said at least two elongated members of said second portion of said clip are adapted to be received by respective clip receiving means of said respective brackets.

91. An orthodontic assembly according to claim 85, wherein said clip is fabricated of a single metal wire member which integrally forms said first and second portions.

92. An orthodontic assembly according to claim 91, wherein said metal wire is an amorphous spring wire.

93. In combination, a wingless orthodontic bracket and a wire spring clip,
the wingless bracket comprising:
  a generally rectangular parallelepiped shaped body member having a front surface, an opposed rear surface adapted to be secured to a tooth, and a pair of opposing side surfaces;
  an arch wire receiving opening formed in a front surface portion of said body member;
  at least one elongated rear groove extending transverse to said arch wire receiving opening and formed in a rear surface portion of said body member; and
  a pair of elongated wire receiving side grooves on respective opposing side surface portions of said body member and extending generally transverse to said arch wire receiving opening; and
said spring clip comprising:
  a first resilient wire portion comprising at least two spaced apart elongated members for engaging and passing over at least a part of said front surface of said bracket and for passing over at least a portion of said arch wire receiving opening to retain an arch wire relative to said bracket, said at least two elongated members being spaced apart a distance so as to pass over a part of said front surface of the bracket and over at least a portion of said arch wire receiving opening intermediate the ends of said elongated arch wire receiving opening;
  a second wire portion comprised of at least two elongated members coupled to said first wire portion of said clip, each of said two members of said second wire portion engaging at least one of said rear groove and side grooves of said bracket when said first wire portion of said clip at least partially covers said arch wire receiving opening of the bracket; and
  means coupling together the elongated members of at least one of said first and second clip portions.

94. An orthodontic bracket according to claim 93, further comprising a pair of grooves in said front surface portion and extending generally transverse to said arch wire receiving opening.

95. An orthodontic bracket according to claim 93, wherein said at least one groove in said rear surface portion further comprises an auxiliary opening extending therefrom for receiving auxiliaries, or the like, therethrough.

96. An orthodontic bracket according to claim 93, comprising respective clip engaging means in communication with said grooves on said opposing side surface portions of said bracket.

97. An orthodontic bracket according to claim 93, further comprising at least two of said elongated grooves formed in said rear surface portion.

98. An orthodontic bracket according to claim 93, comprising at least one through bore in said bracket extending transverse to said arch wire receiving opening.

99. An orthodontic bracket according to claim 93, wherein said rear surface of said bracket comprises three rear grooves therein.

100. An orthodontic bracket according to claim 99, wherein said rear grooves comprise a generally centrally located groove for receiving at least a portion of a spring clip therein.

101. An orthodontic assembly comprising:
an orthodontic bracket means having a front surface portion with an elongated arch wire receiving opening formed in said front surface portion, and spring clip receiving means; and
a wire spring clip comprising:
  a first resilient wire portion comprising at least two spaced apart elongated members for engaging and passing over at least a part of said front surface portion of said bracket having said arch wire receiving opening, said at least two elongated members being spaced apart a distance so as to pass over at least a part of said front surface portion and over at least a portion of said arch wire receiving opening intermediate the ends of said elongated arch wire receiving opening;
  a second wire portion coupled to said first wire portion and including means for engaging said clip receiving means of said bracket when said first wire portion at least partially covers said arch wire receiving opening of the bracket;
  said first and second wire portions comprising means movable relative to said clip receiving means of said bracket so as to permit said first wire portion to be moved relative to said bracket after being mounted on said bracket to less than completely pass over said arch wire receiving opening to permit removal and insertion of an arch wire or the like, in said arch wire receiving opening of the bracket; and
  at least one of said first and second wire portions comprising further engagement means engaging at least a portion of the bracket to prevent said clip from becoming disengaged from said bracket during movement of said clip relative to said bracket to insert or remove an arch wire, or the like, in the arch wire receiving opening of the bracket.

102. An orthodontic spring clip according to claim 101 wherein said second wire portion comprises spring means for resiliently retaining said clip relative to said bracket with said first portion retaining an arch wire, or the like, relative to said bracket, said spring means bearing against said bracket for permitting resilient movement of said spring clip relative to said bracket to permit removal or insertion of said arch wire, or the like, in said bracket.

103. An orthodontic spring clip according to claim 101 wherein said second wire portion comprises at least two elongated members coupled to said first wire portion, and wherein said spring means comprises bowed out portions of said elongated members of said second wire portion, said bowed out portions being spaced from respective surfaces of said bracket when said clip is fully engaged with said bracket.

104. An orthodontic spring clip according to claim 101 wherein said bracket comprises at least one depression therein, and said second wire portion comprises means for engaging said at least one depression, and said spring means comprises a resilient portion of said second wire portion engageable in said depression and slidable along a surface of said depression during movement of said spring clip relative to said bracket, said resilient portion of said second wire portion resiliently yielding during movement of said spring clip relative to said bracket.

105. An orthodontic spring clip according to claim 101 wherein said bracket has an elongated aperture extending therethrough, and said second wire portion extends through said elongated aperture.

106. An orthodontic spring clip according to claim 105 wherein said second wire portion comprises rotation prevention means engageable with said bracket for preventing rotation of said wire clip about the axis of said elongated aperture when said clip is moved relative to said bracket to permit removal or insertion of an arch wire, or the like, in said arch wire receiving opening.

107. An orthodontic spring clip according to claim 106 wherein said rotation prevention means comprises a bent portion of said second wire portion.

108. An orthodontic spring clip according to claim 107 wherein said bent portion is at an end portion of said second wire portion.

109. An orthodontic spring clip according to claim 101 wherein said first and second wire portions comprises portions thereof which are spaced from each other in the axial direction of the arch wire so as to produce torsional bending forces responsive to forces applied thereto by an arch wire, or the like.

110. An orthodontic spring clip according to claim 101 wherein said first wire portion has first and second members passing over at least a portion of said arch wire receiving opening, said first and second members being spaced from each other in the axial direction of the arch wire so as to produce torsional bending forces responsive to forces applied thereto by an arch wire, or the like.

111. An orthodontic clip according to claim 101, wherein said at least two spaced apart elongated members of said first wire portion pass completely over said arch wire receiving opening of the bracket.

112. An orthodontic clip according to claim 101, wherein said second wire portion engages said bracket intermediate the ends of said elongated arch wire receiving opening.

113. An orthodontic assembly comprising:
an orthodontic bracket means having an elongated arch wire receiving opening in a front surface portion thereof, and clip receiving means; and
an orthodontic clip including:
  a first wire portion comprising at least two spaced apart elongated members for engaging and passing over at least a part of said front surface portion of said bracket and for passing over at least a portion of said arch wire receiving opening to retain an arch wire relative to said bracket, said at least two elongated members being spaced apart a distance so as to pass over a part of said front surface portion of said bracket and over at least a portion of said arch wire receiving opening intermediate the ends of said elongated arch wire receiving opening;
  a second wire portion comprised of at least two elongated members coupled to said first wire portion of said clip and including bent-over bracket engaging means at the end portions of said elongated members of said second wire portion for engaging said clip receiving means of said bracket when said first wire portion of said clip at least partially covers said arch wire receiving opening of said bracket; and
  means integrally coupling together the respective elongated members of said first and second wire clip portions, said coupling means interconnecting said elongated members of said first wire portion at the ends thereof remote from said elongated members of said second wire portion, said bentover bracket engaging means being at the ends of said elongated members of said second wire portion which are remote from said first wire portion.

114. An orthodontic assembly comprising:
an orthodontic bracket means having an elongated arch wire receiving opening in a front surface portion thereof, and at least two clip receiving openings; and
an orthodontic clip including:
  a first wire portion comprising at least two spaced apart elongated members for engaging and passing over at least a part of said front surface portion of said bracket and for passing over at least a portion of said arch wire receiving opening to retain an arch wire relative to said bracket, said at least two elongated members being spaced apart a distance so as to pass over a part of said front surface portion of said bracket and over at least a portion of said arch wire receiving opening intermediate the ends of said elongated arch wire receiving opening;
  a second wire portion comprised of at least two elongated members coupled to said first wire portion of said clip, each of said elongated members of said second wire portion including respective means for passing through respective clip receiving openings of said bracket when said first wire portion of said clip at least partially covers said arch wire receiving opening of said bracket; and
  means coupling together the elongated members of at least one of said first and second clip portions.

* * * * *

UNITED STATES PATENT AND TRADEMARK OFFICE
CERTIFICATE OF CORRECTION

PATENT NO. : 4,197,642
DATED : April 15, 1980
INVENTOR(S) : Melvin WALLSHEIN

It is certified that error appears in the above–identified patent and that said Letters Patent are hereby corrected as shown below:

Column 27, line 25, replace "bracket has" with
--clip receiving means includes--.

Signed and Sealed this

Twenty-fourth Day of June 1980

[SEAL]

Attest:

SIDNEY A. DIAMOND

Attesting Officer     Commissioner of Patents and Trademarks